United States Patent
Nord et al.

(10) Patent No.: US 10,398,911 B2
(45) Date of Patent: Sep. 3, 2019

(54) METHOD AND APPARATUS FOR USING A MULTI-LAYER MULTI-LEAF COLLIMATION SYSTEM

(71) Applicant: Varian Medical Systems International AG, Cham (CH)

(72) Inventors: Janne I. Nord, Espoo (FI); Jarkko Y. Peltola, Tuusula (FI); Esa Kuusela, Espoo (FI)

(73) Assignee: Varian Medical Systems Internationl AG, Steinhausen (CH)

( * ) Notice: Subject to any disclaimer, the term of this patent is extended or adjusted under 35 U.S.C. 154(b) by 779 days.

(21) Appl. No.: 14/865,863

(22) Filed: Sep. 25, 2015

(65) Prior Publication Data
US 2017/0087384 A1  Mar. 30, 2017

(51) Int. Cl.
*A61N 5/10* (2006.01)
*G21K 1/04* (2006.01)

(52) U.S. Cl.
CPC ......... *A61N 5/1031* (2013.01); *A61N 5/1045* (2013.01); *G21K 1/046* (2013.01)

(58) Field of Classification Search
CPC ........ A61N 5/10; A61N 5/103; A61N 5/1036; A61N 5/1045; A61N 5/1047; G21K 1/00
See application file for complete search history.

(56) References Cited

U.S. PATENT DOCUMENTS

| | | | | |
|---|---|---|---|---|
| 4,868,844 A * | 9/1989 | Nunan | ............. | G21K 1/046 378/147 |
| 5,591,983 A * | 1/1997 | Yao | ............. | G21F 5/04 250/505.1 |
| 6,335,961 B1 * | 1/2002 | Wofford | ............. | A61N 5/1042 378/151 |
| 6,459,769 B1 * | 10/2002 | Cosman | ............. | A61N 5/1042 250/505.1 |
| 7,015,490 B2 * | 3/2006 | Wang | ............. | A61N 5/1031 250/505.1 |
| 7,180,980 B2 * | 2/2007 | Nguyen | ............. | A61N 5/103 378/148 |
| 7,590,219 B2 * | 9/2009 | Maurer, Jr. | ............. | A61N 5/103 378/145 |
| 7,817,778 B2 * | 10/2010 | Nord | ............. | A61N 5/1047 378/65 |
| 7,894,574 B1 * | 2/2011 | Nord | ............. | A61N 5/1042 378/65 |
| 8,085,899 B2 * | 12/2011 | Nord | ............. | A61N 5/103 378/65 |

(Continued)

*Primary Examiner* — Thomas R Artman
(74) *Attorney, Agent, or Firm* — Fitch, Even, Tabin & Flannery LLP

(57) ABSTRACT

A multi-layer multi-leaf collimation system includes at least a first layer of collimation leaves that are vertically offset with respect to a second layer of collimation leaves. A control circuit generates a preliminary radiation treatment plan using a model of a radiation therapy treatment platform using a single-layer multi-leaf collimation system following which the control circuit generates a final radiation treatment plan that takes into account at least a second layer of collimation leaves. The resultant final radiation treatment plan can then be used to administer radiation to a patient using the aforementioned multi-layer multi-leaf collimation system.

19 Claims, 3 Drawing Sheets

(56) References Cited

U.S. PATENT DOCUMENTS

| | | | | |
|---|---|---|---|---|
| 8,519,370 B2* | 8/2013 | Luzzara | A61N 5/1045 | 250/492.1 |
| 8,637,841 B2* | 1/2014 | Prince | A61N 5/1045 | 250/492.1 |
| 9,082,520 B2* | 7/2015 | Prince | A61N 5/1045 | |
| 9,966,160 B2* | 5/2018 | Kawrykow | A61N 5/1045 | |
| 10,143,859 B2* | 12/2018 | Ollila | A61N 5/1077 | |
| 2005/0123098 A1* | 6/2005 | Wang | A61N 5/1031 | 378/151 |
| 2006/0045238 A1* | 3/2006 | Nguyen | A61N 5/103 | 378/65 |
| 2008/0011945 A1* | 1/2008 | Maurer, Jr. | A61N 5/103 | 250/252.1 |
| 2008/0013687 A1* | 1/2008 | Maurer, Jr. | A61N 5/103 | 378/145 |
| 2008/0123813 A1* | 5/2008 | Maurer | A61N 5/103 | 378/96 |
| 2009/0154644 A1* | 6/2009 | Nord | A61N 5/103 | 378/65 |
| 2010/0054411 A1* | 3/2010 | Nord | A61N 5/1031 | 378/65 |
| 2012/0043482 A1* | 2/2012 | Prince | G21K 1/046 | 250/505.1 |
| 2012/0256103 A1* | 10/2012 | Luzzara | A61N 5/1045 | 250/492.1 |
| 2014/0112453 A1* | 4/2014 | Prince | G21K 1/046 | 378/152 |
| 2014/0217312 A1* | 8/2014 | Echner | A61N 5/1045 | 250/505.1 |
| 2017/0087384 A1* | 3/2017 | Nord | A61N 5/1031 | |
| 2017/0148536 A1* | 5/2017 | Kawrykow | A61N 5/1045 | |
| 2018/0078785 A1* | 3/2018 | Ollila | A61N 5/1036 | |
| 2018/0078792 A1* | 3/2018 | Ollila | A61N 5/1077 | |
| 2018/0161602 A1* | 6/2018 | Kawrykow | A61B 6/03 | |
| 2019/0046815 A1* | 2/2019 | Ollila | A61N 5/1077 | |

* cited by examiner

METHOD AND APPARATUS FOR USING A MULTI-LAYER MULTI-LEAF COLLIMATION SYSTEM

RELATED APPLICATION(S)

This application is related to co-pending and co-owned U.S. patent application Ser. No. 14/865,890, entitled METHOD AND APPARATUS TO EMPLOY A MULTI-LAYER MULTI-LEAF COLLIMATOR WHEN ADMINISTERING A RADIATION THERAPY TREATMENT and filed on even date herewith, which is incorporated by reference in its entirety herein.

TECHNICAL FIELD

These teachings relate generally to the administration of therapeutic doses of radiation and more particularly to the use of multi-leaf collimators.

BACKGROUND

Multi-leaf collimators are comprised of a plurality of individual parts (known as "leaves") that are formed of a high atomic numbered material (such as tungsten) that can move independently in and out of the path of the radiation-therapy beam in order to selectively block (and hence shape) the beam. Typically the leaves of a multi-leaf collimator are organized in pairs that are aligned collinearly with respect to one another and that can selectively move towards and away from one another via controlled motors. A typical multi-leaf collimator has many such pairs of leaves, often upwards of twenty, fifty, or even one hundred such pairs.

By passing a therapeutic radiation beam through the aperture(s) of a multi-leaf collimator the radiation beam can be modulated to better match the dosing requirements of the treatment session. These dosing requirements typically include (or at least presume) prescribing which body tissues to irradiate and which body tissues to avoid irradiating.

While a typical multi-leaf collimator represents an enormous improvement in terms of better shaping a radiation beam to meet such requirements, it nevertheless remains true that, at least some of the time, the resultant beam shape does not perfectly meet such requirements. This shortcoming typically arises as a function of the maximum resolution by which the multi-leaf collimator is able to shape the beam. When the leaves of the multi-leaf collimator have a cross-dimension of, for example, 1.0 centimeter, that is generally orthogonal to the incoming beam, that dimension imposes a corresponding limit as to the resolution capabilities of the collimator.

BRIEF DESCRIPTION OF THE DRAWINGS

The above needs are at least partially met through provision of the method and apparatus for using a multi-layer multi-leaf collimation system described in the following detailed description, particularly when studied in conjunction with the drawings, wherein.

Figure 1:
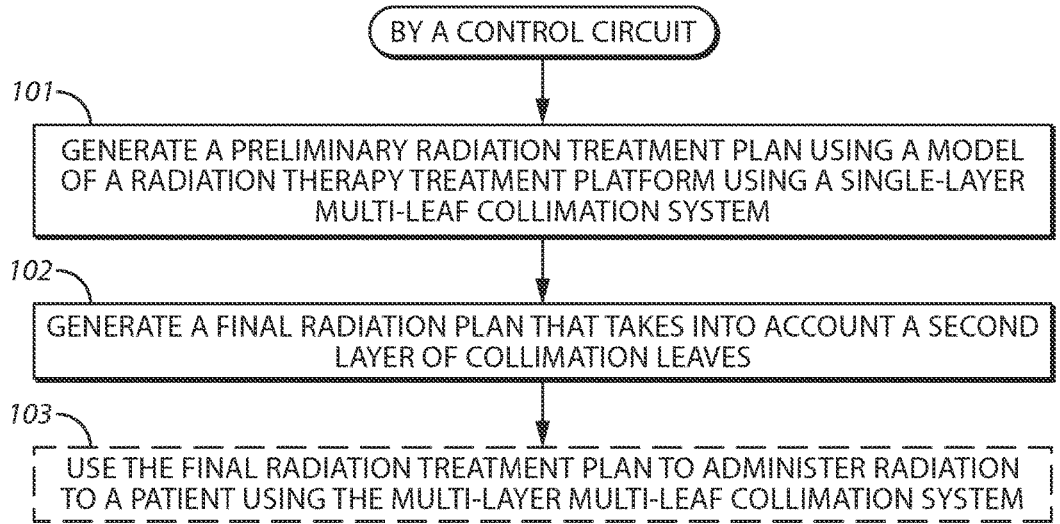
FIG. 1 comprises a flow diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments a multi-layer multi-leaf collimation system includes at least a first layer of collimation leaves that are vertically offset with respect to a second layer of collimation leaves. A control circuit generates a preliminary radiation treatment plan using a model of a radiation therapy treatment platform using a single-layer multi-leaf collimation system following which the control circuit generates a final radiation treatment plan that takes into account at least a second layer of collimation leaves. The resultant final radiation treatment plan can then be used to administer radiation to a patient using the aforementioned multi-layer multi-leaf collimation system.

By one approach the collimation leaves of the first layer of the multi-layer multi-leaf collimation system have a same width as the collimation leaves of the second layer of the multi-layer multi-leaf collimation system. In such a case, if desired, the first layer of collimation leaves are vertically offset with respect to the second layer of collimation leaves by approximately one half the width of the collimation leaves.

By one approach the single-layer multi-leaf collimation system of the model of the radiation therapy treatment platform presumes that the single-layer multi-leaf collimation system has collimation leaves having a width that is less than the width of the collimation leaves of the first and second layer of the multi-layer multi-leaf collimation system. For example, the width of the collimation leaves for the single-layer multi-leaf collimation system can be approximately one half the width of the collimation leaves of the first layer and/or second layer of the multi-layer multi-leaf collimation system.

In lieu of the foregoing or in combination therewith, the single-layer multi-leaf collimation system of the model of the radiation therapy treatment platform can presume that the single-layer multi-leaf collimation system has a greater number of collimation leaves than either of the first layer or the second layer of the multi-layer multi-leaf collimation system (for example, twice as many leaves). Accordingly, by one approach, the single-layer multi-leaf collimation system of the model of the radiation therapy treatment platform can presume that the single-layer multi-leaf collimation system has collimation leaves that are less in width and greater in number than the collimation leaves of the first layer and second layer of the multi-layer multi-leaf collimation system.

When generating the final radiation treatment plan that takes into account a second layer of collimation leaves as per the foregoing, these teachings will accommodate, for example, modifying the preliminary radiation treatment plan to avoid apertures that the multi-layer multi-leaf collimation system cannot produce. In any event, generating the final radiation treatment plan can comprise determining how to produce planned apertures formed by the single-layer multi-leaf collimation system using the multi-layer multi-leaf collimation system.

In lieu of the foregoing, and by another approach, these teachings will accommodate presuming that the collimation leaves of the single-layer multi-leaf collimation system have better transmission parameters than the collimation leaves of either the first layer or the second layer of the multi-layer multi-leaf collimation system. In such a case, generating the final radiation treatment plan that takes into account a second layer of collimation leaves can comprise, at least in part, refining apertures that are defined in the preliminary radiation treatment plan to provide higher resolution by optimizing collimation leaf positions in the second layer of collimation leaves.

So configured, these approaches help address the deficiencies of prior art optimization techniques that do not work well with two or more layers of multi-leaf collimators. In particular, the present teachings can greatly aid in leveraging such additional layers to improve the definition and/or resolution of beam-shaping apertures. Such improvements, in turn, can further help to assure that treatment targets receive a desired radiation dosage while non-targeted surrounding areas receive less unwanted radiation.

Figure 2:
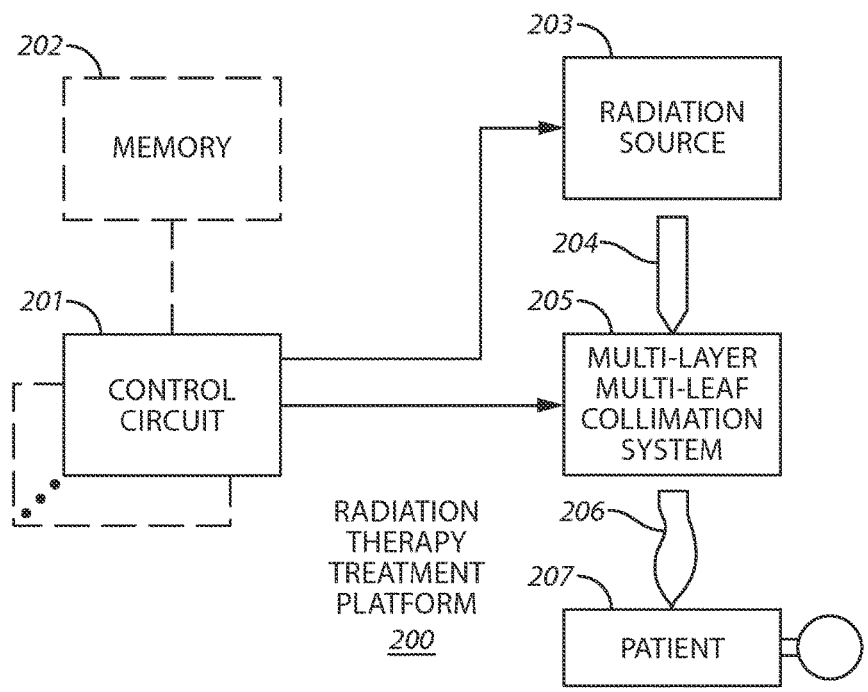
FIG. 2 comprises a block diagram as configured in accordance with various embodiments of these teachings.

These and other benefits may become clearer upon making a thorough review and study of the following detailed description. Referring now to the drawings, and in particular to FIG. 1, an illustrative process 100 that is compatible with many of these teachings will now be presented. For the sake of an illustrative example it is presumed here in that a control circuit of choice carries out the steps, actions, and/or functionality of this process 100. FIG. 2 presents an illustrative example in this regard.

As shown in FIG. 2, a radiation therapy treatment platform 200 can include or otherwise operably couple to a control circuit 201. Being a "circuit," the control circuit 201 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 201 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 201 is configured (for example, by using corresponding programming as will be well understood by those skilled in the art) to carry out one or more of the steps, actions, and/or functions described herein. It will also be understood that a "control circuit" can comprise multiple such components or platforms as well as suggested by the phantom control circuit box in FIG. 2.

By one optional approach the control circuit 201 operably couples to a memory 202. This memory 202 may be integral to the control circuit 201 or can be physically discrete (in whole or in part) from the control circuit 201 as desired. This memory 202 can also be local with respect to the control circuit 201 (where, for example, both share a common circuit board, chassis, power supply, and/or housing) or can be partially or wholly remote with respect to the control circuit 201 (where, for example, the memory 202 is physically located in another facility, metropolitan area, or even country as compared to the control circuit 201).

In addition to radiation treatment plans this memory 202 can serve, for example, to non-transitorily store the computer instructions that, when executed by the control circuit 201, cause the control circuit 201 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

The radiation therapy treatment platform 200 also includes a radiation source 203 that operably couples and responds to the control circuit 201. So configured, the corresponding radiation beam 204 as emitted by the radiation source 203 can be selectively switched on and off by the control circuit 201. These teachings will also accommodate having the control circuit 201 control the relative strength of the radiation beam 204. Radiation sources are well understood in the art and require no further description here.

The radiation beam 204 is directed towards a multi-layer multi-leaf collimation system 205 that also operably couples to the control circuit 201 to thereby permit the control circuit 201 to control movement of the collimation systems leaves and hence the formation and distribution of one or more radiation-modulating apertures. The resultant modulated radiation beam 206 then reaches a treatment target in a corresponding patient 207.

Figure 3:
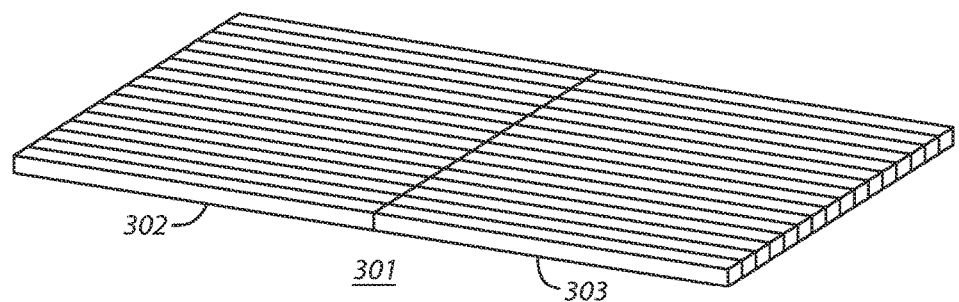
FIG. 3 comprises a perspective schematic view as configured in accordance with various embodiments of these teachings.

FIG. 3 presents a representative view of a first layer 301 of collimating leaves for the multi-layer multi-leaf collimating system 205. Generally speaking this first layer 301 includes a plurality of selectively movable collimating leaves 302 that each comprise a first leaf for a corresponding pair of collimating leaves. This first layer 301 also includes a second plurality of selectively movable collimating leaves 303 that each comprise a second leaf for the aforementioned pair of collimating leaves. So configured, when one or both collimating leaves as comprise a pair of collimating leaves are selectively moved away from one another, a beam-shaping aperture forms therebetween. (The manner by which electric motors can be employed to effect such movement comprises a well understood area of prior art endeavor. Accordingly, for the sake of brevity, additional details in those regards are not provided here.)

The second layer of collimating leaves for the multi-layer multi-leaf collimating system 205 can be identical to the first layer 301 described above. Or, if desired, these teachings will accommodate a variety of relatively small changes. For example, the second layer of collimating leaves may include one or more additional pairs of collimating leaves or one or more fewer pairs of collimating leaves as compared to the first layer 301. As another example, the collimating leaves of the second layer may be somewhat greater in width or somewhat lesser in width than the collimating leaves of the first layer 301.

Figure 4:
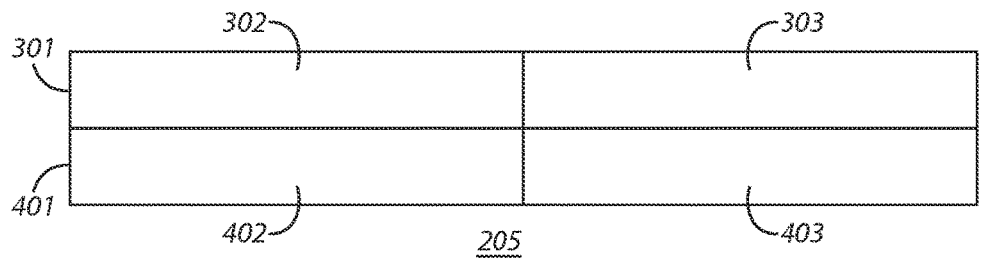
FIG. 4 comprises a front elevational schematic view as configured in accordance with various embodiments of these teachings.

In any event, and as generally represented in FIG. 4, the first layer 301 and second layer 401 of the collimating leaves are generally juxtaposed one atop the other (with or without some amount of intervening space as desired). In this example the first layer 301 comprises a so-called proximal layer and hence is oriented towards the aforementioned radiation source 203. Accordingly, the second layer 401 comprises a so-called distal layer that is oriented opposite the radiation source 203 and towards the patient 207.

In this illustrative example the collimating leaves of the first layer 301 are generally laterally aligned with the collimating leaves of the second layer 401. For example, the left side (as illustrated) collimating leaves 302 for the first layer 301 are laterally aligned with the left side collimating leaves 402 of the second layer 401. Similarly, the right side (as illustrated) collimating leaves 303 of the first layer 301 are laterally aligned with the right side collimating leaves 403 of the second layer 401. These teachings are highly flexible in practice and will accommodate other orientations and juxtapositions as may be useful to address the needs of a specific application setting. For example, it may be useful in some cases to laterally offset the collimating leaves of one layer from the collimating leaves of the other layer.

Figure 5:
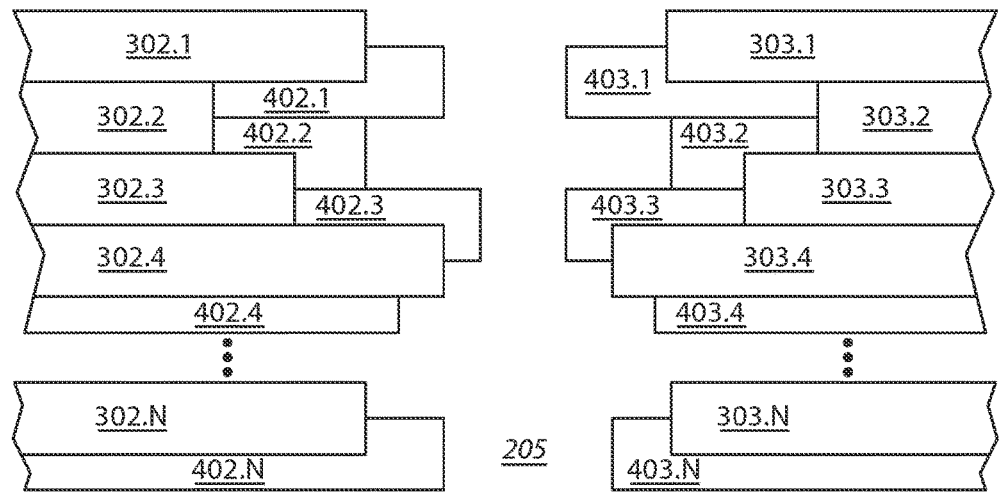
FIG. 5 comprises a top plan view as configured in accordance with various embodiments of these teachings.

Although the collimating leaves for these two layers 301 and 401 may be laterally aligned, as shown in FIG. 5 the collimation leaves for these two layers 301 and 401 are vertically offset with respect to one another. (It will be understood that the word "vertically" as used herein refers to the orientation context shown in these illustrations. In an application setting the multi-layer multi-leaf collimation system 205 can be oriented in any of a variety of ways. Accordingly, it will be further understood that the word "vertically" as used herein refers to the relative context of the collimation leaves when the multi-layer multi-leaf collimation system 205 itself is oriented vertically and upright which will not necessarily correlate to the orientation of the system in a particular application setting.)

Accordingly, it can be seen that the left-side collimating leaves 302.1-302.N (where "N" is an integer) of the first layer 301 each only partially overlap the left-side collimating leaves 402.1-402.N of the second layer 401. Similarly, the right-side collimating leaves 303.1-303.N of the first layer 301 each only partially overlap the right-side collimating leaves 403.1-403.N of the second layer 401. In the illustrated example the collimating leaves of each layer are offset vertically by fifty percent and accordingly the first layer 301 has collimating leaves that each overlap corresponding leaves of the second layer 401 by fifty percent as well. In this example the various leaves are depicted with the leaves of each leaf pair having been opened to some greater or lesser extent to facilitate better viewing of the collimating leaves of the second layer 401.

Figure 6:
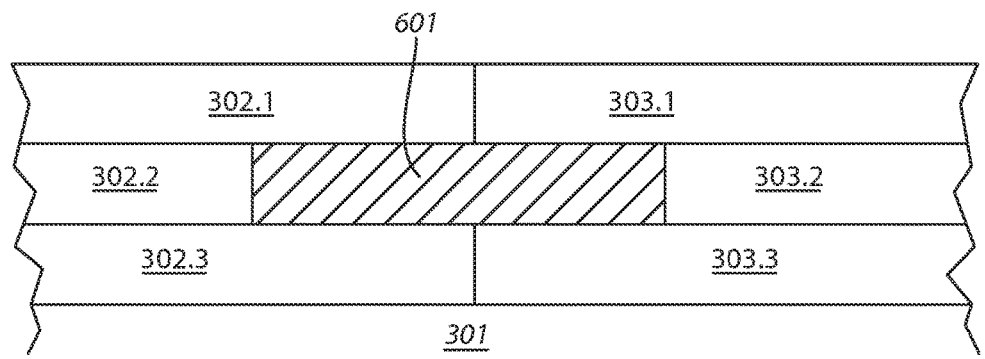
FIG. 6 comprises a top plan view as configured in accordance with various embodiments of these teachings.
Figure 7:
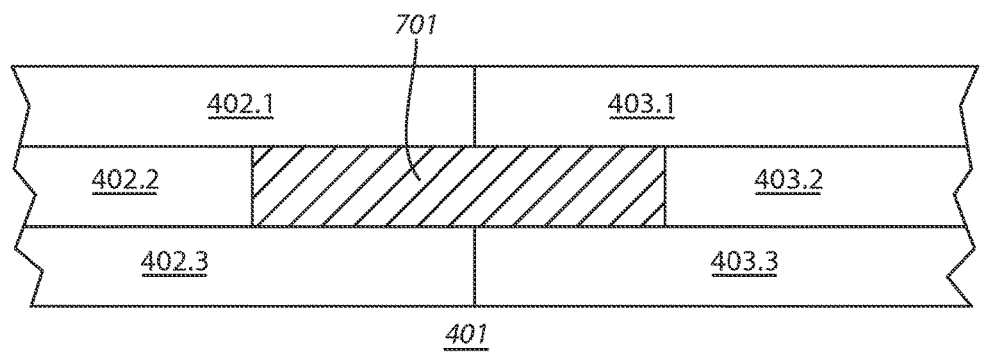
FIG. 7 comprises a top plan view as configured in accordance with various embodiments of the invention.
Figure 8:
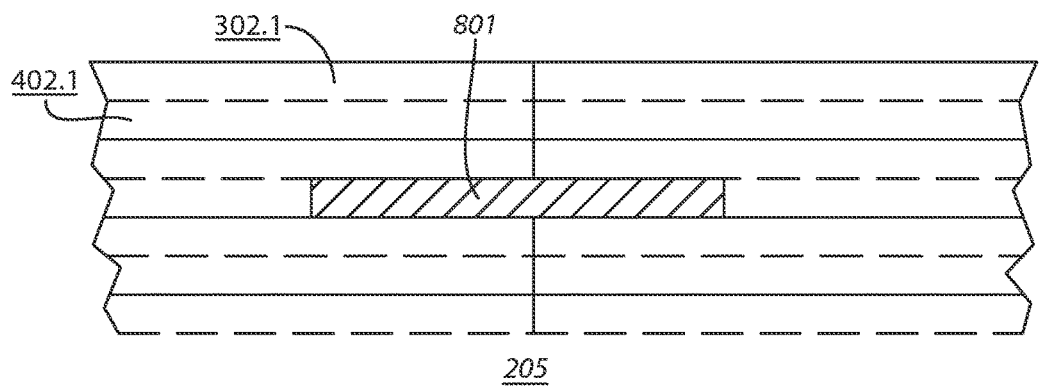
FIG. 8 comprises a top plan view as configured in accordance with various embodiments of these teachings.

The applicant has determined that the aperture resolution capable of a multi-leaf collimator can be significantly increased by employing such a multi-layer multi-leaf collimator 205. FIGS. 6-8 provide an illustrative example in these regards. FIG. 6 depicts an aperture 601 formed using collimating leaves of the first layer 301. In this simple example, a pair of collimating leaves 302.2 and 303.2 have been moved away from one another while the collimating leaves above and below that pair of collimating leaves remain closed to form that aperture 601. Necessarily, this aperture 601 has a vertical dimension identical to the vertical dimensions of that pair of collimating leaves.

FIG. 7 presents an aperture 701 formed in an identical manner to that just described, albeit using collimating leaves of the second layer 401. Again, the resultant aperture 701 has a vertical dimension that is necessarily identical to the vertical dimensions of the collimating leaves.

FIG. 8 illustrates the aperture 801 that results when the two layers 301 and 401 are stacked one atop the other in an offset manner as described above. Accordingly, the two apertures 601 and 701 described above only partially overlap one another to form this resultant aperture 801. In this particular illustrative example the aperture 801 has a vertical dimension that is only one half the vertical dimension of the collimating leaves. Accordingly, this particular approach yields a 2× improvement in aperture resolution in these regards. That improvement in resolution provides an opportunity to more precisely shape a radiation beam 204 to match the contours of a given treatment target.

With continued reference to the foregoing illustrations, and in particular to FIGS. 1 and 2, this process 100 provides, at block 101, for generating a preliminary radiation treatment plan using a model of a radiation therapy treatment platform that uses a single-layer multi-leaf collimation system rather than the above-described multi-layer multi-leaf collimation system 205. As is well understood in the art, generating a radiation treatment plan typically relies upon models for one or more aspects of the radiation therapy treatment platform. It is also well understood that generating a radiation treatment plan often entails making use of iterative optimization processes. As used herein, "optimization" will be understood to refer to improving a treatment plan without necessarily ensuring that the optimized result is, in fact, the singular best solution. Such optimization often includes automatically adjusting one or more treatment parameters (often while observing one or more corresponding limits in these regards) and mathematically calculating a likely corresponding treatment result to identify a given set of treatment parameters that represent a good compromise between the desired therapeutic result and avoidance of undesired collateral effects. Since optimization practices themselves are a well-understood area of prior art endeavor, further details are not provided here in these regards for the sake of brevity and simplicity.

That said, it will be well appreciated that a model for a single-layer multi-leaf collimation system will typically be considerably less complex than a model for a multi-layer multi-leaf collimation system and hence will typically permit a corresponding iterative optimization process to resolve to a solution (in this case, the aforementioned preliminary radiation treatment plan) more quickly.

By one approach the single-layer multi-leaf collimation system of the model of the radiation therapy treatment platform presumes that the single-layer multi-leaf collimation system has collimation leaves having a height (or width, depending upon the viewing context) that is less than the height/width of the collimation leaves of the first layer 301 and the second layer 401 of the multi-layer multi-leaf collimation system 205. When the two layers 301 and 401 of the multi-layer multi-leaf collimation system 205 are vertically offset by one half the height/width of the individual leaves, by one approach the collimation leaves for the single-layer multi-leaf collimation system have a width/height that is approximately one half the width/height of the collimation leaves for the multi-layer multi-leaf collimation system 205.

Accordingly, by one approach the single-layer multi-leaf collimation system of the model of the radiation therapy treatment platform can further presume that the single-layer multi-leaf collimation system has a greater number of collimation leaves than either of the first layer 301 and second layer 401 of the multi-layer multi-leaf collimation system 205. For example, when the overlap is approximately fifty percent as described above, the single-layer multi-leaf collimation system can be presumed to have approximately twice as many collimation leaves as either of the first layer 301 and the second layer 401 of the multi-layer multi-leaf collimation system 205. (As used herein, this reference to "approximately" will be understood to refer to small variations such as plus or minus one to five leaves in systems using twenty to one hundred leaves.)

In any event, the single-layer multi-leaf collimation system of the aforementioned model of the radiation therapy treatment platform will typically be presumed to have collimation leaves that are less in width/height and greater in number than the collimation leaves of the first layer 301 and second layer 401 of the multi-layer multi-leaf collimation system 205.

At block 102 the control circuit 201 then uses the aforementioned preliminary radiation treatment plan to generate a final radiation treatment plan by now taking into account a second layer of collimation leaves. As one simple example in these regards, this activity can comprise, at least in part, modifying the preliminary radiation treatment plan to avoid apertures that the multi-layer multi-leaf collimation system 205 cannot produce (either at all under any circumstances or under the particular circumstances dictated by the plan).

As another example in these regards, the control circuit 201 can take into account a second layer of collimation leaves by, at least in part, determining how to produce the planned apertures to be formed by the single-layer multi-leaf collimation system using the multi-layer multi-leaf collimation system. By one approach the control circuit 201 can make these determinations by again employing an iterative optimization process that tests and evaluates a variety of different leaf positions for both the first and second layers 301 and 401 of the multi-layer multi-leaf collimation system 205.

Although the foregoing approach essentially concatenates two separate optimization processes, the overall time required to achieve a good solution using the disclosed approach can be considerably less than an approach that presumes initially the use of a multi-layer multi-leaf collimation system and attempts at the outset to optimize a plan employing such a system.

It shall be understood that the foregoing process 100 is quite flexible in practice and will modify variations, modifications, or even substitutions as regards the foregoing details. As one example in these regards, if desired the collimation leaves of the single-layer multi-leaf collimation system for the model of the radiation therapy treatment platform can be presumed to have better transmission parameters than the collimation leaves of either the first layer 300 and one or second layer 401 of the multi-layer multi-leaf collimation system 205. As an illustrative example in these regards, "better" could mean having twice the attenuation power (i.e., if one layer of multi-layer collimator material lets 1% of the radiation come through, then two layers will let 0.01 times 0.01 come through. Accordingly the transmission factor for the virtual one-layered multi-layer collimator could be 0.0001 instead of 0.01).

In this case, the aforementioned generation of the final radiation treatment plan that takes into account a second layer of collimation leaves can comprise, at least in part, refining the apertures defined in the preliminary radiation treatment plan to provide higher resolution by optimizing collimation leaf positions in the second layer 401 of collimation leaves.

At optional block 103 this process 100 provides for using the aforementioned final radiation treatment plan to administer radiation to a patient 207 using the multi-layer multi-leaf collimation system 205. This activity can include, for example, selectively moving various leaves of the first and second layers 301 and 401 of the multi-layer multi-leaf collimation system 205 to form one or more apertures for single or multiple exposures on a per-field basis as desired.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A method for use with a radiation therapy treatment platform having a multi-layer multi-leaf collimation system wherein a first layer of collimation leaves are laterally offset with respect to a second layer of collimation leaves, the method comprising:
    by a control circuit:
        generating a preliminary radiation treatment plan using a model of a radiation therapy treatment platform comprising a single-layer multi-leaf collimation system having a single layer of collimation leaves that may be the same as or different than the first layer or the second layer of collimation leaves of the multi-layer multi-leaf collimation system;
        using the preliminary radiation treatment plan to generate a final radiation treatment plan for the radiation therapy treatment platform that takes into account at least two layers of collimation leaves.

2. The method of claim 1 wherein the collimation leaves of the first layer have a same width as the collimation leaves of the second layer, and wherein the single-layer multi-leaf collimation system of the model of the radiation therapy treatment platform presumes that the single-layer multi-leaf collimation system has collimation leaves having a width that is less than the width of the collimation leaves of the first layer and the second layer.

3. The method of claim 2 wherein the width of the collimation leaves for the single-layer multi-leaf collimation system is approximately one half the width of the collimation leaves of the first layer and the second layer.

4. The method of claim 1 wherein the single-layer multi-leaf collimation system of the model of the radiation therapy treatment platform presumes that the single-layer multi-leaf collimation system has a greater number of collimation leaves than either of the first layer and the second layer.

5. The method of claim 4 wherein the single-layer multi-leaf collimation system of the model of the radiation therapy treatment platform presumes that the single-layer multi-leaf collimation system has at least twice as many collimation leaves as the first layer or the second layer.

6. The method of claim 1 wherein the single-layer multi-leaf collimation system of the model of the radiation therapy treatment platform presumes that the single-layer multi-leaf collimation system has collimation leaves that are less in width and greater in number than the collimation leaves of the first layer and the second layer.

7. The method of claim 6 wherein generating the final radiation treatment plan that takes into account a second layer of collimation leaves comprises, at least in part, modifying the preliminary radiation treatment plan to avoid apertures that the multi-layer multi-leaf collimation system cannot produce.

8. The method of claim 6 wherein generating the final radiation treatment plan that takes into account a second layer of collimation leaves comprises, at least in part, determining how to produce planned apertures formed by the single-layer multi-leaf collimation system using the multi-layer multi-leaf collimation system.

9. The method of claim 8 further comprising:
using the final radiation treatment plan to administer radiation to a patient using the multi-layer multi-leaf collimation system.

10. The method of claim 1 wherein the collimation leaves of the single-layer multi-leaf collimation system are presumed to have better transmission parameters than the collimation leaves of either the first layer or the second layer.

11. The method of claim 10 wherein generating the final radiation treatment plan that takes into account a second layer of collimation leaves comprises, at least in part, refining apertures defined in the preliminary radiation treatment plan to provide higher resolution by optimizing collimation leaf positions in the second layer of collimation leaves.

12. An apparatus comprising:
a control circuit configured to generate a radiation treatment plan by:
generating a preliminary version of the radiation treatment plan using a model of a radiation therapy treatment platform comprising a single-layer multi-leaf collimation system;
using the preliminary version of the radiation treatment plan to generate a final version of the radiation treatment plan that takes into account a second layer of collimation leaves.

13. The apparatus of claim 12 further comprising:
a multi-layer multi-leaf collimation system wherein a first layer of collimation leaves are laterally offset with respect to a second layer of collimation leaves, wherein the collimation leaves of the first layer have a same width as the collimation leaves of the second layer; and
wherein the single-layer multi-leaf collimation system of the model of the radiation therapy treatment platform presumes that the single-layer multi-leaf collimation system has collimation leaves having a width that is less than the width of the collimation leaves of the first layer and the second layer and that the single-layer multi-leaf collimation system has a greater number of collimation leaves than either of the first layer and the second layer.

14. The apparatus of claim 13 wherein the width of the collimation leaves for the single-layer multi-leaf collimation system is approximately one half the width of the collimation leaves of the first layer and the second layer.

15. The apparatus of claim 13 wherein the control circuit is configured to generate the final radiation treatment plan that takes into account a second layer of collimation leaves by, at least in part, modifying the preliminary radiation treatment plan to avoid apertures that the multi-layer multi-leaf collimation system cannot produce.

16. The method of claim 15 wherein the control circuit is configured to generate the final radiation treatment plan that takes into account a second layer of collimation leaves by, at least in part, determining how to produce planned apertures formed by the single-layer multi-leaf collimation system using the multi-layer multi-leaf collimation system.

17. The apparatus of claim 16 further comprising:
a radiation therapy treatment platform configured to use the final radiation treatment plan to administer radiation to a patient using the multi-layer multi-leaf collimation system.

18. The apparatus of claim 12 wherein the collimation leaves of the single-layer multi-leaf collimation system are presumed to have better transmission parameters than the collimation leaves of a multi-layer multi-leaf collimation system.

19. The apparatus of claim 18 wherein the control circuit is configured to generate the final radiation treatment plan that takes into account a second layer of collimation leaves by, at least in part, refining apertures defined in the preliminary radiation treatment plan to provide higher resolution by optimizing collimation leaf positions in the second layer of collimation leaves.

* * * * *

UNITED STATES PATENT AND TRADEMARK OFFICE
CERTIFICATE OF CORRECTION

PATENT NO. : 10,398,911 B2  
APPLICATION NO. : 14/865863  
DATED : September 3, 2019  
INVENTOR(S) : Janne I. Nord, Jarkko Y. Peltola and Esa Kuusela Page 1 of 1

It is certified that error appears in the above-identified patent and that said Letters Patent is hereby corrected as shown below:

On the Title Page

(73) Assignee: delete "Internationl" and insert --International--.

Signed and Sealed this  
Twenty-ninth Day of October, 2019

Andrei Iancu  
*Director of the United States Patent and Trademark Office*